(12) United States Patent
Reese et al.

(10) Patent No.: US 9,297,732 B2
(45) Date of Patent: Mar. 29, 2016

(54) METHOD AND APPARATUS FOR TESTING SUPERHARD MATERIAL PERFORMANCE

(75) Inventors: Michael R. Reese, Houston, TX (US); Alfazazi Dourfaye, Paris (FR)

(73) Assignee: VAREL EUROPE S.A.S., Batiment D Pau (FR)

( * ) Notice: Subject to any disclaimer, the term of this patent is extended or adjusted under 35 U.S.C. 154(b) by 1506 days.

(21) Appl. No.: 12/967,893

(22) Filed: Dec. 14, 2010

(65) Prior Publication Data

US 2011/0148021 A1 Jun. 23, 2011

Related U.S. Application Data

(60) Provisional application No. 61/288,143, filed on Dec. 18, 2009.

(51) Int. Cl.
*G01N 3/58* (2006.01)
*G01N 3/56* (2006.01)

(52) U.S. Cl.
CPC .. *G01N 3/58* (2013.01); *G01N 3/56* (2013.01); *G01N 2203/0266* (2013.01); *G01N 2203/0298* (2013.01); *Y10T 408/03* (2015.01); *Y10T 428/21* (2015.01); *Y10T 428/219* (2015.01); *Y10T 428/2933* (2015.01); *Y10T 428/2978* (2015.01)

(58) Field of Classification Search
CPC ....................................................... B23P 19/04
See application file for complete search history.

(56) References Cited

U.S. PATENT DOCUMENTS

| | | | |
|---|---|---|---|
| 4,233,064 A * | 11/1980 | Dunn, Jr. ........................ 75/526 |
| 4,442,494 A | 4/1984 | Fromson et al. |
| 5,154,245 A | 10/1992 | Waldenstrom et al. |
| 5,641,921 A | 6/1997 | Dennis et al. |
| 6,003,623 A | 12/1999 | Miess |
| 6,238,448 B1 | 5/2001 | Rouse et al. |
| 6,412,330 B1 | 7/2002 | Dicello et al. |
| 6,695,073 B2 | 2/2004 | Glass et al. |
| 2006/0006588 A1 * | 1/2006 | Winget et al. ................. 264/544 |
| 2006/0027745 A1 * | 2/2006 | Rebettge et al. ............... 250/292 |

(Continued)

FOREIGN PATENT DOCUMENTS

| | | |
|---|---|---|
| JP | H081523 | 1/1996 |
| SU | 918075 | 7/1982 |
| WO | 9623952 | 8/1996 |

OTHER PUBLICATIONS

Ken Bertagnolli and Roger Vale, Understanding and Controlling Residual Stresses in Thick Polycrystalline Diamond Cutters For Enhanced Durability, 9 pages, US Synthetic Corporation, Orem, Utah.

(Continued)

*Primary Examiner* — Lee D Wilson (57) ABSTRACT

A target cylinder and a method for fabricating the target cylinder. The target cylinder includes a first end, a second end, and a sidewall extending from the first end to the second end. At least one of the second end and the sidewall is an exposed portion that makes contact with a superhard component to determine at least one property of the superhard component. The exposed portion comprises at least one soft material and at least one hard material that is interveningly positioned between or within the soft material in a predetermined and repeatable pattern. In one embodiment, the differential of the unconfined compressive strength between the hard material and the soft material ranges from about 1,000 psi to about 60,000 psi.

12 Claims, 6 Drawing Sheets

(56) References Cited

U.S. PATENT DOCUMENTS

2007/0192074 A1    8/2007  Chen
2011/0100960 A1*   5/2011  Rebettge .................... 219/69.17
2011/0148021 A1*   6/2011  Reese et al. ................... 269/287

OTHER PUBLICATIONS

B. A. Eaton, A. B. Bower Jr., and J. A. Martis, Manufactured Diamond Cutters Used in Drilling Bits, May 1975, Journal of Petroleum Technology, pp. 543-551, American Institute of Mining, Metallurgical, and Petroleum Engineers, Inc., Houston, Texas.

William C. Maurer, Advanced Drilling Techniques, Chapter 22: Stratapax Bits, The Petroleum Publishing Company, Jun. 1980, pp. 541-590.

Young, Lee W, International Search Report and Written Opinion of the International Searching Authority for PCT/US2010/060305, Feb. 28, 2011, pp. 1-11.

* cited by examiner

METHOD AND APPARATUS FOR TESTING SUPERHARD MATERIAL PERFORMANCE

CROSS-REFERENCE TO RELATED APPLICATIONS

This application claims priority to U.S. Provisional Patent Application No. 61/288,143, entitled "Method and Apparatus for Testing Superhard Material Performance," filed Dec. 18, 2009, the entirety of which is incorporated by reference herein.

TECHNICAL FIELD

The present invention relates generally to a method and apparatus for testing superhard components; and more particularly, to a method and apparatus for testing the abrasive wear resistance and/or the impact resistance of superhard components.

BACKGROUND

Figure 1:
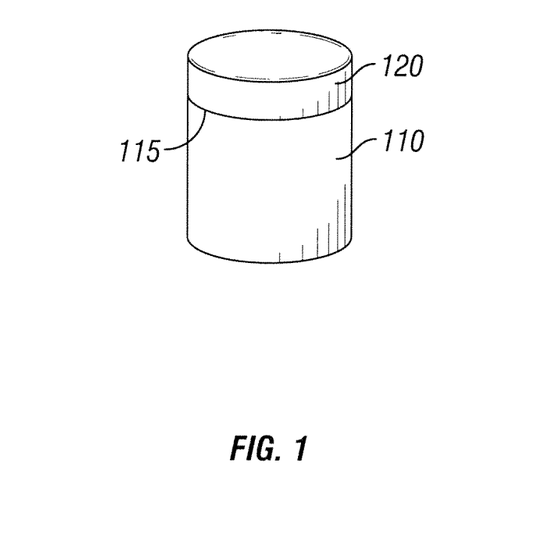
FIG. 1 shows a superhard component that is insertable within a downhole tool in accordance with an exemplary embodiment of the invention.

FIG. 1 shows a superhard component 100 that is insertable within a downhole tool (not shown) in accordance with an exemplary embodiment of the invention. One example of a superhard component 100 is a cutting element 100, or cutter, for rock bits. The cutting element 100 typically includes a substrate 110 having a contact face 115 and a cutting table 120. The cutting table 120 is fabricated using an ultra hard layer which is bonded to the contact face 115 by a sintering process. The substrate 110 is generally made from tungsten carbide-cobalt, or tungsten carbide, while the cutting table 120 is formed using a polycrystalline ultra hard material layer, such as polycrystalline diamond ("PCD") or polycrystalline cubic boron nitride ("PCBN"). These cutting elements 100 are fabricated according to processes and materials known to persons having ordinary skill in the art.

Common problems associated with these cutters 100 include chipping, spalling, partial fracturing, cracking, and/or flaking of the cutting table 120. These problems result in the early failure of the cutting table 120. Typically, high magnitude stresses generated on the cutting table 120 at the region where the cutting table 120 makes contact with earthen formations during drilling can cause these problems. These problems increase the cost of drilling due to costs associated with repair, production downtime, and labor costs. For these reasons, testing methods have been developed to ascertain the abrasion resistance and/or impact resistance of cutters 100 so that improved cutter longevity is achieved and the problems discussed above are substantially reduced.

Figure 2:
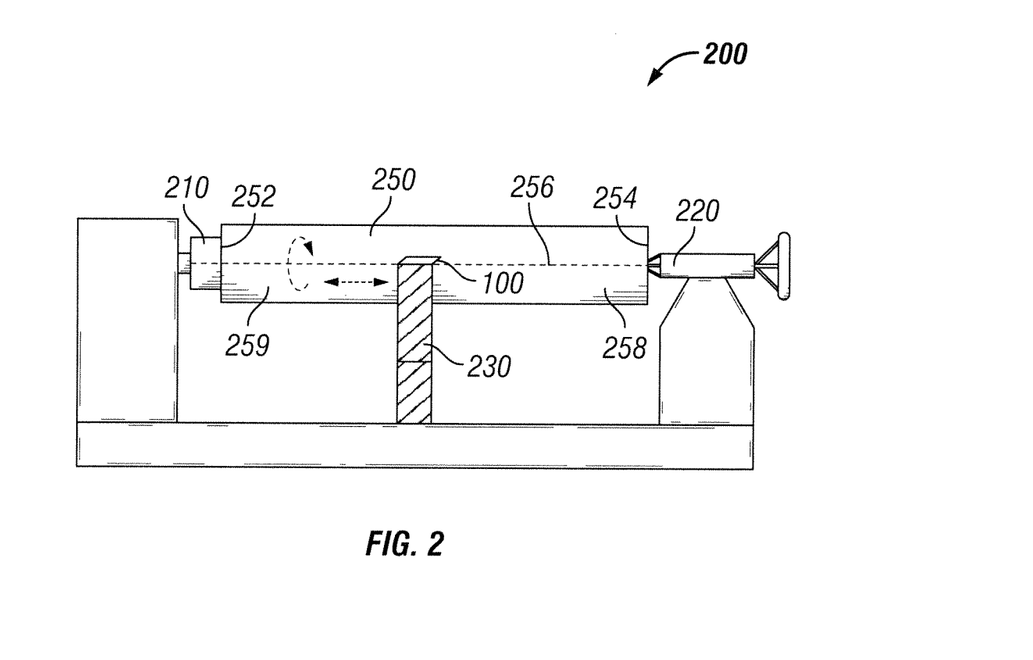
FIG. 2 shows a lathe for testing abrasive wear resistance using a conventional granite log test.

Superhard components 100, which include polycrystalline diamond compact ("PDC") cutters 100, have been tested for abrasive wear resistance through the use of two conventional testing methods. The PDC cutter 100 includes the cutting table 120 fabricated from polycrystalline diamond. FIG. 2 shows a lathe 200 for testing abrasive wear resistance using a conventional granite log test. Although one exemplary apparatus configuration for the lathe 200 is provided, other apparatus configurations can be used without departing from the scope and spirit of the exemplary embodiment.

Referring to FIG. 2, the lathe 200 includes a chuck 210, a tailstock 220, and a tool post 230 positioned between the chuck 210 and the tailstock 220. A target cylinder 250 has a first end 252, a second end 254, and a sidewall 258 extending from the first end 252 to the second end 254. According to the conventional granite log test, sidewall 258 is an exposed surface 259 which makes contact with the superhard component 100 during the test. The first end is coupled to the chuck 210, while the second end 254 is coupled to the tailstock 220. The chuck 210 is configured to rotate, thereby causing the target cylinder 250 to also rotate along a central axis 256 of the target cylinder 250. The tailstock 220 is configured to hold the second end 254 in place while the target cylinder 250 rotates. The target cylinder 250 is fabricated from a single uniform material, which is typically granite. However, other single uniform rock types have been used for the target cylinder 250, which includes, but is not limited to, Jackforck sandstone, Indiana limestone, Berea sandstone, Carthage marble, Champlain black marble, Berkley granite, Sierra white granite, Texas pink granite, and Georgia gray granite. These target cylinders 250 are costly to acquire, shape, ship, and handle.

The PDC cutter 100 is fitted to the lathe's tool post 230 so that the PDC cutter 100 makes contact with the target cylinder's 250 exposed surface 259 and drawn back and forth across the exposed surface 259. The tool post 230 has an inward feed rate on the target cylinder 250. The abrasive wear resistance for the PDC cutter 100 is determined as a wear ratio, which is defined as the volume of target cylinder 250 that is removed to the volume of the PDC cutter 100 that is removed. Alternatively, instead of measuring volume, the distance that the PDC cutter 100 travels across the target cylinder 250 can be measured and used to quantify the abrasive wear resistance for the PDC cutter 100. Alternatively, other methods known to persons having ordinary skill in the art can be used to determine the wear resistance using the granite log test. Operation and construction of the lathe 200 is known to people having ordinary skill in the art. Descriptions of this type of test is found in the Eaton, B. A., Bower, Jr., A. B., and Martis, J. A. "Manufactured Diamond Cutters Used In Drilling Bits." *Journal of Petroleum Technology*, May 1975, 543-551. Society of Petroleum Engineers paper 5074-PA, which was published in the Journal of Petroleum Technology in May 1975, and also found in Maurer, William C., *Advanced Drilling Techniques*, Chapter 22, The Petroleum Publishing Company, 1980, pp. 541-591, which is incorporated by reference herein. This granite log test was adequate during the initial stages of PDC cutter 100 development. However, PDC cutters 100 have become more resistant to abrasive wear as the technology for PDC cutters 100 improved. Current technology PDC cutters 100 are capable of cutting through many target cylinders 250 without ever developing any appreciable and measurable wear flat; thereby, making the conventional granite log test method inefficient and too costly for measuring the abrasive wear resistance of superhard components 100.

Figure 3:
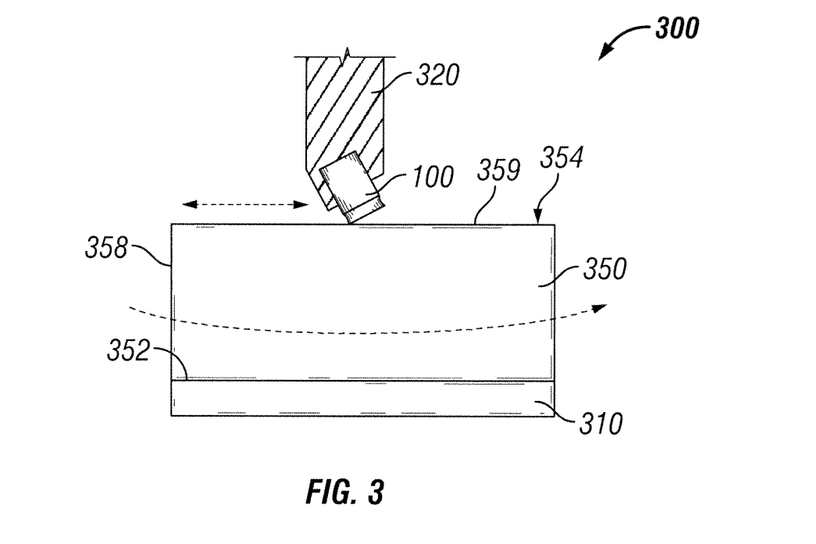
FIG. 3 shows a vertical boring mill for testing abrasive wear resistance using a vertical boring mill test or vertical turret lathe test.

FIG. 3 shows a vertical boring mill 300 for testing abrasive wear resistance using a vertical boring mill ("VBM") test or vertical turret lathe ("VTL") test. Although one exemplary apparatus configuration for the VBM 300 is provided, other apparatus configurations can be used without departing from the scope and spirit of the exemplary embodiment. The vertical boring mill 300 includes a rotating table 310 and a tool holder 320 positioned above the rotating table 310. A target cylinder 350 has a first end 352, a second end 354, and a sidewall 358 extending from the first end 352 to the second end 354. According to the conventional VBM test, second end 354 is an exposed surface 359 which makes contact with a superhard component 100 during the test. The target cylinder 350 is typically about thirty inches to about sixty inches in diameter.

The first end 352 is mounted on the lower rotating table 310 of the VBM 300, thereby having the exposed surface 359 face the tool holder 320. The PDC cutter 100 is mounted in the tool holder 320 above the target cylinder's 350 exposed surface 359 and makes contact with the exposed surface 359. The target cylinder 350 is rotated as the tool holder 320 cycles the PDC cutter 100 from the center of the target cylinder's 350 exposed surface 359 out to its edge and back again to the center of the target cylinder's 350 exposed surface 359. The tool holder 320 has a predetermined downward feed rate. The VBM method allows for higher loads to be placed on the PDC cutter 100 and the larger target cylinder 350 provides for a greater rock volume for the PDC cutter 100 to act on. The target cylinder 350 is typically fabricated entirely from granite; however, the target cylinder can be fabricated entirely from another single uniform material that includes, but is not limited to, Jackforck sandstone, Indiana limestone, Berea sandstone, Carthage marble, Champlain black marble, Berkley granite, Sierra white granite, Texas pink granite, and Georgia gray granite. As previously mentioned, these target cylinders 350 are costly to acquire, shape, ship, and handle.

Figure 10:
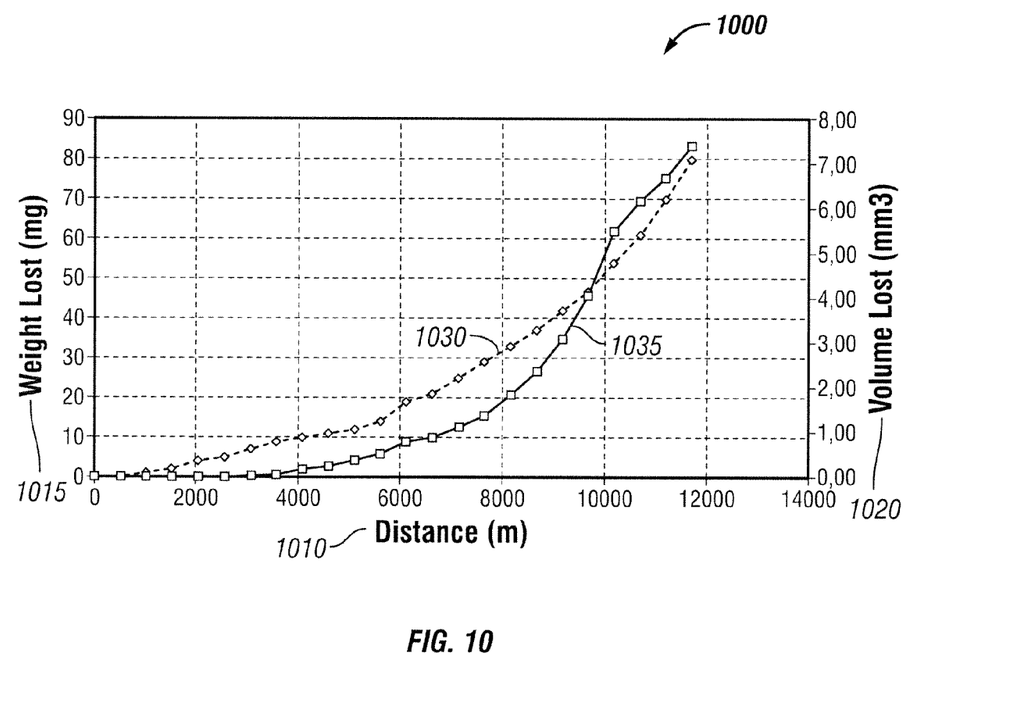
FIG. 10 shows a graphical wear curve representation using conventional target cylinders.

The abrasive wear resistance for the PDC cutter 100 is determined as a wear ratio, which is defined as the volume of target cylinder 350 that is removed to the volume of the PDC cutter 100 that is removed. Alternatively, instead of measuring volume, the distance that the PDC cutter 100 travels across the target cylinder 350 can be measured and used to quantify the abrasive wear resistance for the PDC cutter 100. FIG. 10 shows a graphical wear curve representation 1000 using conventional target cylinders 250 and 350 (FIGS. 2 and 3).

Referring to FIG. 10, the graphical wear curve representation 1000 has a distance travelled x-axis 1010, a weight lost y-axis 1015, and a volume lost y-axis 1020. The distance travelled x-axis 1010 represents the distance that the PDC cutter 100 (FIG. 1) travels across the conventional target cylinder 250 and 350 (FIGS. 2 and 3) and is measured in meters. The weight lost y-axis 1015 represents the weight that the conventional target cylinder 250 and 350 loses as the PDC cutter 100 travels across the conventional target cylinder 250 and 350 and is measured in milligrams. The volume lost y-axis 1020 represents the volume that the conventional target cylinder 250 and 350 loses as the PDC cutter 100 travels across the conventional target cylinder 250 and 350 and is measured in cubic millimeters. The relationship between the distance travelled by the PDC cutter 100 and the weight lost by the conventional target cylinder 250 and 350 is illustrated by a distance and weight curve 1030. The relationship between the distance travelled by the PDC cutter 100 and the volume lost by the conventional target cylinder 250 and 350 is illustrated by a distance and volume curve 1035. Both the distance and weight curve 1030 and the distance and volume curve 1035 are provided based upon the following parameters: 1) 13.4 millimeter PDC cutter diameter; 2) 2 millimeter depth of cut; and 3) a 1.8 meters per second average linear speed. As seen in the graphical wear curve representation 1000, both the distance and weight curve 1030 and the distance and volume curve 1035 have uniform increasing wear because the conventional target cylinder 250 and 350 is fabricated using a uniform material and the effect of any impact of the PDC cutter 100 on the conventional target cylinder 250 and 350 is minimized.

Alternatively, other methods known to persons having ordinary skill in the art can be used to determine the wear resistance using the VBM test. Operation and construction of the VBM 300 is known to people having ordinary skill in the art. A description for this type of testing can be found in Bertagnolli, Ken and Vale, Roger, "Understanding and Controlling Residual Stresses in Thick Polycrystalline Diamond Cutters for Enhanced Durability," US Synthetic Corporation, 2000, which is incorporated by reference in its entirety herein.

Figure 4:
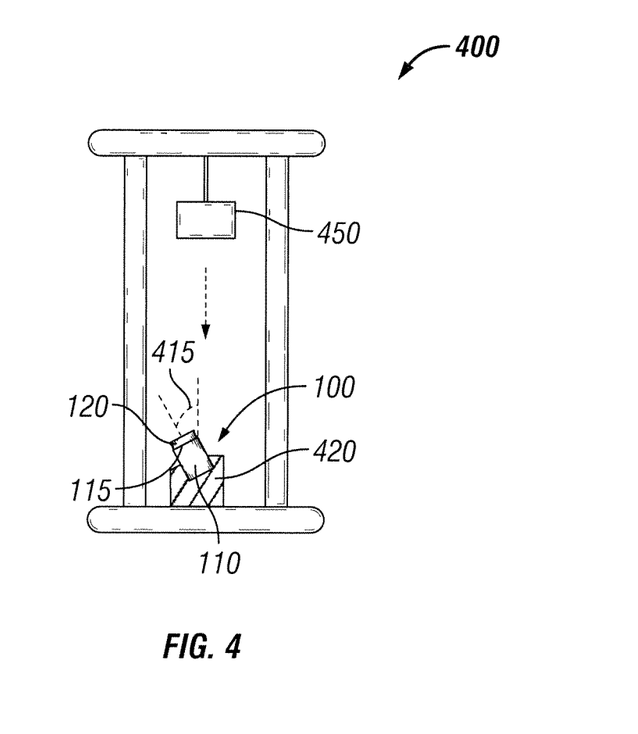
FIG. 4 shows a drop tower apparatus for testing impact resistance of superhard components using a "drop test" method.

In addition to testing for abrasive wear resistance, PDC cutters 100 can also tested for resistance to impact loading. FIG. 4 shows a drop tower apparatus 400 for testing impact resistance of superhard components using a "drop test" method. The drop test method attempts to emulate the type of loading that can be encountered when the PDC cutter 100 transitions from one formation to another or experiences lateral and axial vibrations.

Referring to FIG. 4, the drop tower apparatus 400 includes a superhard component 100, such as a PDC cutter, a target fixture 420, and a strike plate 450 positioned above the superhard component 100. The PDC cutter 100 is locked into the target fixture 420. The strike plate 450, or weight, is typically fabricated from steel and is positioned above the PDC cutter 100. However, the strike plate 450 can be fabricated from alternative materials known to persons having ordinary skill in the art. The PDC cutter 100 is typically held at a backrake angle 415 with the diamond table 120 of the PDC cutter 100 angled upward towards the strike plate 450. The range for the backrake angle 415 is known to people having ordinary skill in the art.

The strike plate 450 is repeatedly dropped down on the edge of the PDC cutter 100 until the edge of the PDC cutter 100 breaks away or spalls off. These tests are also referred to as "side impact" tests because the strike plate 450 impacts an exposed edge of the diamond table 120. Failures typically appear in either the diamond table 120 or at the contact face 115 between the diamond table 120 and the carbide substrate 110. The "drop test" method is very sensitive to the edge geometry of the diamond table 120. If the table 120 is slightly chamfered, the test results can be altered considerably. The total energy, expressed in Joules, expended to make the initial fracture in the diamond table 120 is recorded. For more highly impact resistant cutters 100, the strike plate 450 can be dropped according to a preset plan from increasing heights to impart greater impact energy on the cutter 100 to achieve failure. However, this "drop test" method embodies drawbacks in that this method requires that many cutters 100 be tested to achieve a valid statistical sampling that can compare the relative impact resistance of one cutter type to another cutter type. The test is inadequate in providing results that reflect the true impact resistance of the entire cutter 100 as it would see impact loads in a downhole environment. The test exhibits a static impact effect whereas the true impact is dynamic. The number of impacts per second can be as high as 100 hertz ("Hz").

In view of the foregoing, there is a need in the art for providing an improved testing method for abrasive wear resistance of a superhard component. There also is a need in the art for providing an improved testing method for impact resistance of a superhard component. Further, there is a need in the art for providing testing methods for abrasive wear resistance and/or impact resistance of a superhard component that is repeatable, efficient, and more economical.

BRIEF DESCRIPTION OF THE DRAWINGS

The foregoing and other features and aspects of the invention are best understood with reference to the following description of certain exemplary embodiments, when read in conjunction with the accompanying drawings, wherein.

The drawings illustrate only exemplary embodiments of the invention and are therefore not to be considered limiting of its scope, as the invention may admit to other equally effective embodiments.

BRIEF DESCRIPTION OF EXEMPLARY EMBODIMENTS

The present invention is directed to a method and apparatus for testing the abrasive wear resistance and/or the impact resistance of superhard components. Although the description of exemplary embodiments is provided below in conjunction with a PDC cutter, alternate embodiments of the invention may be applicable to other types of superhard components including, but not limited to, PCBN cutter or other superhard components known or not yet known to persons having ordinary skill in the art.

Figure 5:
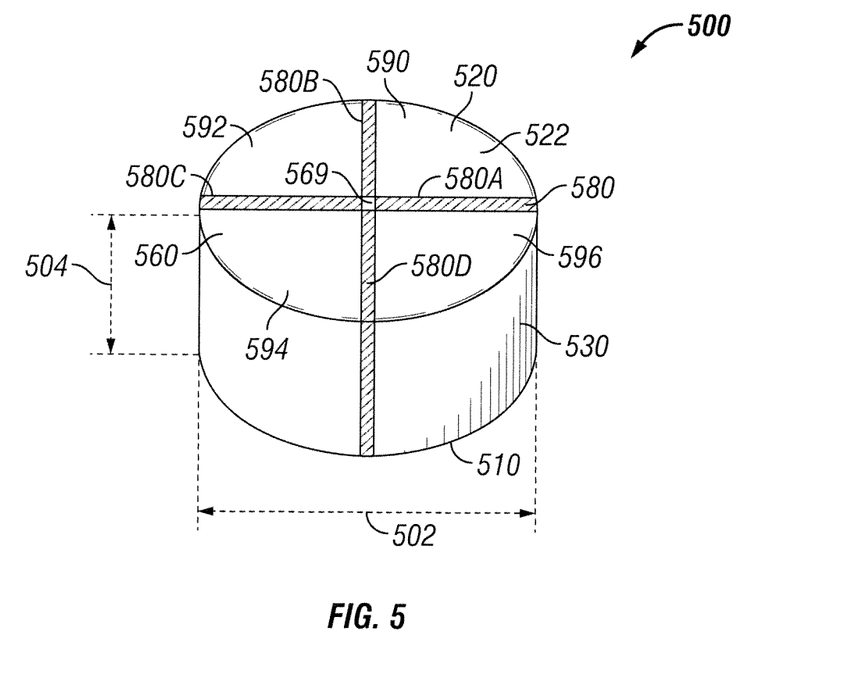
FIG. 5 shows a top perspective view of a target cylinder in accordance with an exemplary embodiment of the invention.

The invention is better understood by reading the following description of non-limiting, exemplary embodiments with reference to the attached drawings, wherein like parts of each of the figures are identified by like reference characters, and which are briefly described as follows. FIG. 5 shows a top perspective view of a target cylinder 500 in accordance with an exemplary embodiment of the invention. Referring to FIG. 5, the target cylinder 500 is cylindrically shaped and includes a first end 510, a second end 520, and a sidewall 530 extending from the first end 510 to the second end 520. According to this exemplary embodiment, the second end 520 is also referred to as an exposed portion 522 of the target cylinder 500 because the second end 520 is subjected to contact with the superhard component 100 (FIG. 1) when the testing is performed. The exposed portion 522 is substantially planar. Although the target cylinder 500 is cylindrically shaped, the target cylinder 500 can be any other geometric or non-geometric shape without departing from the scope and spirit of the exemplary embodiment. The target cylinder 500 has a diameter 502 of approximately three feet and a height 504 of approximately four inches. However, in alternate exemplary embodiments, the diameter 502 can range from about four inches to about six feet without departing from the scope and spirit of the exemplary embodiment. Additionally, in alternate exemplary embodiments, the height 504 can range from about one inch to about twenty feet without departing from the scope and spirit of the exemplary embodiment.

The target cylinder 500 includes a soft material 560 and a hard material 580 that is positioned in a predetermined pattern along the exposed portion 522, wherein the hard material 580 is adjacent to and intervening within the soft material 560. The fabrication of the target cylinder 500 is repeatable so that an initially formed target cylinder 500 is substantially similar to a subsequently formed target cylinder 500. The predetermined pattern for the hard material 580 is repeatable so that the test results can be compared between tests conducted over time. According to FIG. 5, the hard material 580 is a granite slab that is about ¾ inches, or about twenty millimeters, wide and extends from the exposed portion 522 to the first end 510. Although this exemplary embodiment uses a granite slab that is about ¾ inches, or about twenty millimeters, the width of the slabs can vary from about ⅕ inches, or about five millimeters, to about twelve inches in other exemplary embodiments or can also vary in width from one slab to another without departing from the scope and spirit of the exemplary embodiment. Additionally, although the hard material 580 is shaped in substantially rectangular slabs, the hard material 580 can be shaped in any other geometric or non-geometric shape without departing from the scope and spirit of the exemplary embodiment. Examples of hard material 580 include, but are not limited to, sandstone, limestone, marble, granite, wood, plastic, epoxy, and other materials known to people having ordinary skill in the art. In alternative exemplary embodiments, the hard material 580 can extend from the exposed portion 522 to a distance that is a portion of the height 504 without departing form the scope and spirit of the exemplary embodiment. In this exemplary embodiment, there are four pieces of hard material 580A, 580B, 580C, and 580D, where each of the hard materials 580A, 580B, 580C, and 580D are oriented to divide the exposed portion 522 into a first quadrant 590, a second quadrant 592, a third quadrant 594, and a fourth quadrant 596. Hence, the hard material 580 is positioned in an "X-like" pattern.

Specifically, hard material 580A is positioned at substantially ninety degrees to hard material 580D and hard material 580B. Hard material 580B is positioned at substantially ninety degrees to hard material 580A and hard material 580C. Hard material 580C is positioned at substantially ninety degrees to hard material 580B and hard material 580D. Hard material 580D is positioned at substantially ninety degrees to hard material 580C and hard material 580A. Thus, four equally sized quadrants 590, 592, 594, and 596 are formed; however, the angles between the hard materials 580A, 580B, 580C, and 580D can be varied so at least one quadrant is sized differently that the other quadrants. Although four quadrants 590, 592, 594, and 596 are formed at the exposed portion 522, greater or fewer quadrants can be formed at the exposed portion 522 by using more or less hard material 580 slabs positioned interveningly between the soft material 560 without departing from the scope and spirit of the exemplary embodiment. Optionally, the hard material 580 can be oriented in a manner where a soft material core 569 is formed at substantially the center of the target cylinder 500. Although not illustrated, alternatively, the hard material 580 can be oriented in a manner where hard material 580 also is positioned at substantially the center of the target cylinder 500.

The soft material 560 forms the first quadrant 590, the second quadrant 592, the third quadrant 594, and the fourth quadrant 596. The soft material 560 is any moldable rock, rock-like material, or cement-like material, including, but not limited to, mixtures having quartzidic sand and/or other materials known to people having ordinary skill in the art. The soft material 560 optionally can have additives included therein. The soft material 560 may be designed to form a highly abrasive material. According to this exemplary embodiment, the soft material 560 also extends from the exposed portion 522 to the first end 510.

In one exemplary embodiment, the hard material 580 is a granite having an unconfined compressive strength of approximately 12,000 pounds per square inch ("psi") and the soft material 560 is a concrete mixture having an unconfined compressive strength of approximately 5,000 psi. Although examples of material types have been provided for the hard material 580 and the soft material 560, the types of material used for the hard material 580 and the soft material 560 can be any numerous material types so long that the difference of unconfined compressive strength between the hard material 580 and the soft material 560 ranges from about 1,000 psi to about 60,000 psi. In other exemplary embodiments, the difference of unconfined compressive strength between the hard material 580 and the soft material 560 ranges from about 4,000 psi to about 60,000 psi. In other exemplary embodiments, the difference of unconfined compressive strength between the hard material 580 and the soft material 560 ranges from about 6,000 psi to about 60,000 psi. In other exemplary embodiments, the difference of unconfined compressive strength between the hard material 580 and the soft material 560 ranges from about 10,000 psi to about 60,000 psi. In other exemplary embodiments, the difference of unconfined compressive strength between the hard material 580 and the soft material 560 ranges from about 15,000 psi to about 60,000 psi.

In this exemplary embodiment, hard materials 580A, 580B, 580C, and 580D are fabricated from the same material. However, according to certain alternative exemplary embodiments, one or more of hard materials 580A, 580B, 580C, and 580D can be made from a different hard material. Thus, each of hard materials 580A, 580B, 580C, and 580D can be made from a different hard material or one or more of hard materials 580A, 580B, 580C, and 580D can be made from the same hard material without departing from the scope and spirit of the exemplary embodiment.

Similarly, in this exemplary embodiment, each of the first quadrant 590, the second quadrant 592, the third quadrant 594, and the fourth quadrant 596 are formed from the same soft material 560. However, according to certain alternative exemplary embodiments, one or more of the first quadrant 590, the second quadrant 592, the third quadrant 594, and the fourth quadrant 596 can be made from a different soft material 560. Thus, each of the first quadrant 590, the second quadrant 592, the third quadrant 594, and the fourth quadrant 596 can be made from a different soft material 560 or one or more of the first quadrant 590, the second quadrant 592, the third quadrant 594, and the fourth quadrant 596 can be made from the same soft material 560 without departing from the scope and spirit of the exemplary embodiment.

The surface area of the target cylinder's 500 exposed portion 522 is a combination of the soft material 560 and the hard material 580. In one exemplary embodiment, the percentage range of soft material 560 is about five percent to about ten percent, while the percentage range of hard material 580 is about ninety percent to about ninety-five percent. In another exemplary embodiment, the percentage range of soft material 560 is about ten percent to about twenty-five percent, while the percentage range of hard material 580 is about seventy-five percent to about ninety percent. In another exemplary embodiment, the percentage range of soft material 560 is about twenty percent to about thirty-five percent, while the percentage range of hard material 580 is about sixty-five percent to about eighty percent. In another exemplary embodiment, the percentage range of soft material 560 is about thirty percent to about forty-five percent, while the percentage range of hard material 580 is about fifty-five percent to about seventy percent. In another exemplary embodiment, the percentage range of soft material 560 is about forty percent to about fifty-five percent, while the percentage range of hard material 580 is about forty-five percent to about sixty percent. In another exemplary embodiment, the percentage range of soft material 560 is about fifty percent to about sixty-five percent, while the percentage range of hard material 580 is about thirty-five percent to about fifty percent. In another exemplary embodiment, the percentage range of soft material 560 is about sixty percent to about seventy-five percent, while the percentage range of hard material 580 is about twenty-five percent to about forty percent. In another exemplary embodiment, the percentage range of soft material 560 is about seventy percent to about eighty-five percent, while the percentage range of hard material 580 is about fifteen percent to about thirty percent. In another exemplary embodiment, the percentage range of soft material 560 is about eighty percent to about ninety percent, while the percentage range of hard material 580 is about ten percent to about twenty percent. In another exemplary embodiment, the percentage range of soft material 560 is about ninety percent to about ninety-five percent, while the percentage range of hard material 580 is about five percent to about ten percent.

The target cylinder 500 is formed by obtaining a casting form (not shown) and positioning the hard material 580 upright within the casting form in a predetermined pattern. According to one exemplary embodiment, the casting form is cylindrical; however, the casting form can be any other geometric or non-geometric shape. The casting form is filled with a slurry of abrasive material (not shown), such as cement mixed with quartzite grains, so that it surrounds at least a portion of the hard material 580. The slurry of abrasive material is allowed to harden, thereby forming the soft material 560. Once hardened, the casting form is removed and the exposed portion 522 is made smooth and substantially planar. In certain exemplary embodiments, especially where the hard material 580 proceeds through a portion of the target cylinder's 500 height 504, the exposed portion 522 can be end positioned towards the bottom of the casting form.

Alternatively, the target cylinder 500 is formed by obtaining a casting form (not shown) and filling it with a slurry of abrasive material (not shown), such as cement mixed with quartzite grains. According to one exemplary embodiment, the casting form is cylindrical; however, the casting form can be any other geometric or non-geometric shape. The slurry of abrasive material is allowed to harden, thereby forming the soft material 560. The soft material 560 is then slotted or drilled in a predetermined pattern to accept the hard material 580 therein. The hard material 580 is inserted upright into the slots and bonded to the soft material 560 using a bonding material known to people having ordinary skill in the art, such as cement. The casting form is removed and the exposed portion 522 is made smooth and substantially planar.

Alternatively, the target cylinder 500 is formed by obtaining a block of natural abrasive rock, such as Jackfork sandstone, which functions as the soft material 560. The soft material 560 is then slotted or drilled in a predetermined pattern to accept the hard material 580 therein. The hard material 580 is inserted upright into the slots and bonded to the soft material 560 using a bonding material known to people having ordinary skill in the art, such as cement. The casting form is removed and the exposed portion 522 is made smooth and substantially planar. Although some examples have been provided for forming the target cylinder 500, other methods known to people having ordinary skill in the art and having the benefit of the present disclosure can be used without departing from the scope and spirit of the exemplary embodiment.

Once target cylinder 500 is formed, the target cylinder 500 can be used in the VBM test as described above. The target cylinder's 500 first end is coupled to the rotating table 310 (FIG. 3), thereby positioning the exposed portion 522 adjacent the tool holder 320 (FIG. 3) that has the cutter 100 (FIG. 3) mounted therein. Upon performing the VBM test using target cylinder 500, the abrasive wear resistance and/or the impact resistance for the PDC cutter 100 (FIG. 3) can be determined. During the test, the cutter 100 (FIG. 3) repeatedly makes transitions between higher compressive strength material, or hard material 580, and lower compressive strength material, or soft material 560. Each time the cutter 100 (FIG. 3) engages the end of one of the hard material 580, a front impact load is imparted to the cutting table 120 (FIG. 1) and substrate 110 (FIG. 1) as it passes across the hard material 580. When the cutter 100 (FIG. 3) exits hard material 580 and enters the soft material 560, the compressive stress on the cutting table 120 is unloaded or released, thereby creating a rebound test of the substrate 110 (FIG. 1) to the cutting table 120 (FIG. 1) at the contact face 115 (FIG. 1). These occurrences are shown in more detail with respect to FIGS. 11 and 12.

Figure 11:
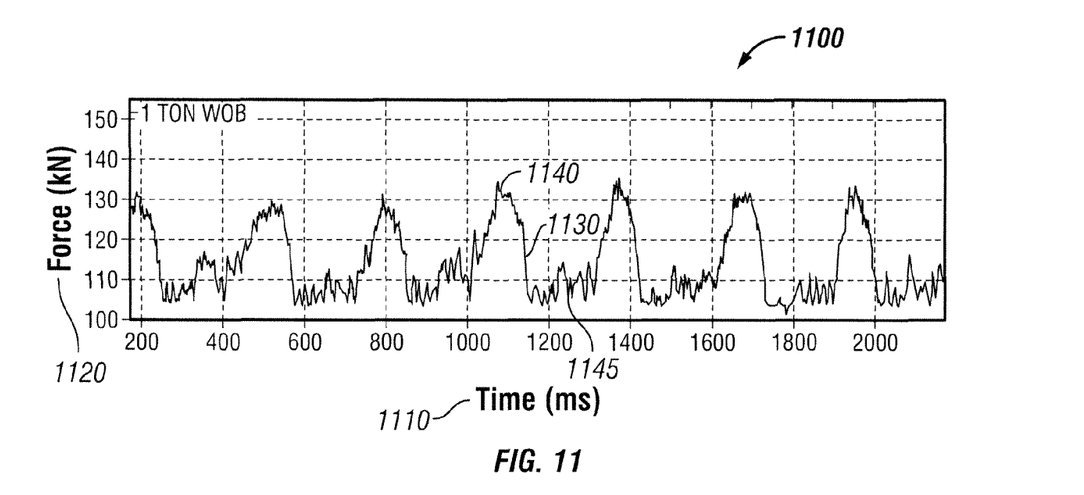
FIG. 11 shows a graphical cyclical cutter load representation using a target cylinder in accordance with an exemplary embodiment of the invention.

FIG. 11 shows a graphical cyclical cutter load representation 1100 using a target cylinder 500, 600, 700, 800, and 900 (FIGS. 5, 6, 7, 8, and 9) in accordance with an exemplary embodiment of the invention. As previously mentioned, each of target cylinders 500, 600, 700, 800, and 900 is fabricated using a combination of hard material and soft material, wherein the hard material is positioned in a predetermined and repeatable pattern with respect to the soft material. Referring to FIG. 11, the graphical cyclical cutter load representation 1100 has a time x-axis 1110 and a force y-axis 1120. The time x-axis 1110 represents the elapsed time, in milliseconds, that the PDC cutter 100 (FIG. 1) has travelled. According to this exemplary embodiment, measurements were taken at fifty hertz. However, measurements can be taken at other frequencies including, but not limited to, frequencies within the range of one hertz to about one hundred hertz. The force y-axis 1120 represents the force, or loading, applied on the PDC cutter 100 and is measured in kilonewtons. The relationship between the elapsed time the PDC cutter 100 has travelled and the force applied onto the PDC cutter 100 is illustrated by a cyclical force curve 1130. The cyclical force curve 1130 shows a peak loading 1140 occurring when the PDC cutter 100 travels across hard material and a low loading 1145 occurring when the PDC cutter 100 travels across soft material.

Figure 12:
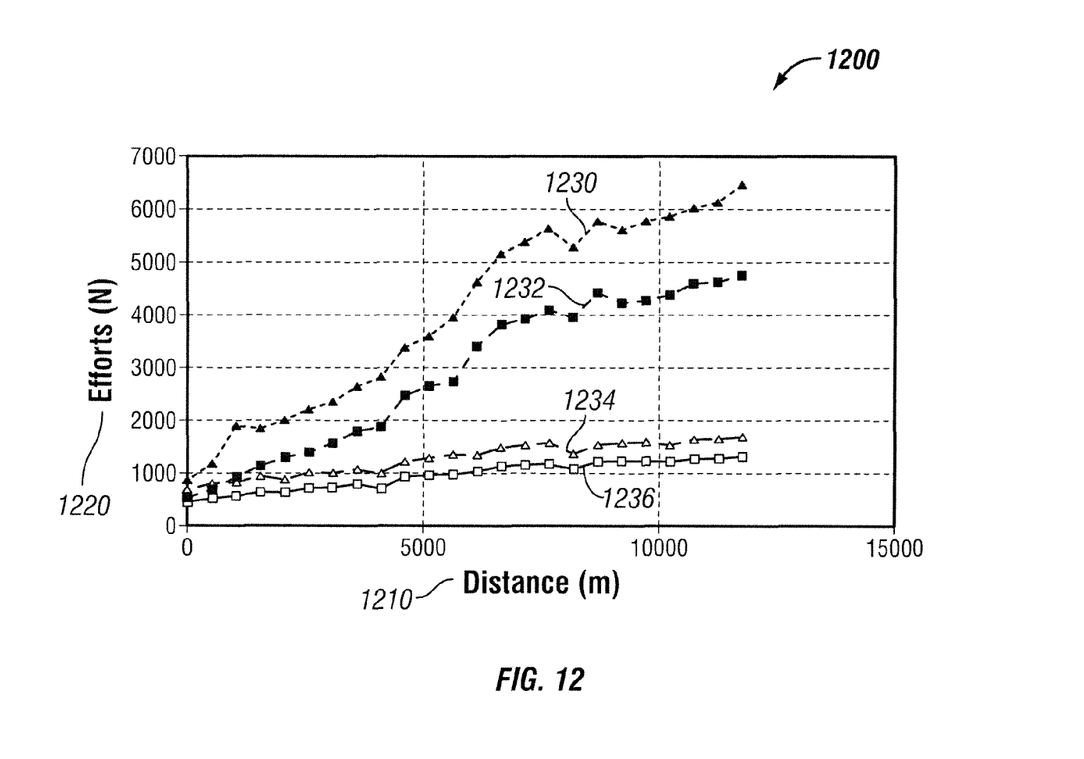
FIG. 12 shows a graphical cutter loading representation using a target cylinder in accordance with an exemplary embodiment of the invention.

FIG. 12 shows a graphical cutter loading representation 1200 using a target cylinder 500, 600, 700, 800, and 900 (FIGS. 5, 6, 7, 8, and 9) in accordance with an exemplary embodiment of the invention. Referring to FIG. 12, the graphical cutter loading representation 1200 has a distance travelled x-axis 1210 and a force y-axis 1220. The distance travelled x-axis 1210 represents the distance that the PDC cutter 100 (FIG. 1) travels across the target cylinder 500, 600, 700, 800 and 900 and is measured in meters. The force y-axis 1220 represents the force, or loading, applied on the PDC cutter 100 and is measured in newtons. The force applied on the PDC cutter 100 includes a normal force and a drag force. The relationship between the distance travelled by the PDC cutter 100 and the maximum normal force applied onto the PDC cutter 100 is illustrated by a maximum normal force curve 1230. The relationship between the distance travelled by the PDC cutter 100 and the average normal force applied onto the PDC cutter 100 is illustrated by an average normal force curve 1232. The relationship between the distance travelled by the PDC cutter 100 and the maximum drag force applied onto the PDC cutter 100 is illustrated by a maximum drag force curve 1234. The relationship between the distance travelled by the PDC cutter 100 and the average drag force applied onto the PDC cutter 100 is illustrated by an average drag force curve 1236. The maximum normal force curve 1230, the average normal force curve 1232, the maximum drag force curve 1234, and the average drag force curve 1236 are provided based upon the following parameters: 1) 13.4 millimeter PDC cutter diameter; 2) 2 millimeter depth of cut; and 3) a 1.8 meters per second average linear speed. As seen in the graphical cutter loading representation 1200, the normal and drag forces applied onto the PDC cutter 100, by the target cylinder 500, 600, 700, 800 and 900 are similar to the forces that the PDC cutter 100 experiences within a wellbore (not shown). It can be seen that the forces applied is not always incrementally higher as the PDC cutter 100 travels a further distance.

Referring back to FIG. 5, the abrasive wear resistance is determined as a wear ratio, which is defined as the volume of target cylinder 500 that is removed to the volume of the PDC cutter 100 (FIG. 3) that is removed. Alternatively, instead of measuring volume, the distance that the PDC cutter 100 (FIG. 3) travels across the target cylinder 500 can be measured and used to quantify the abrasive wear resistance for the PDC cutter 100 (FIG. 3). Alternatively, other methods known to persons having ordinary skill in the art can be used to determine the wear resistance using the VBM test. Impact resistance for the PDC cutter 100 (FIG. 3) also can be determined using the same test by measuring the volume of diamond removed from the PDC cutter 100 (FIG. 3) through chipage. Alternatively, the impact resistance for the PDC cutter 100 (FIG. 3) can be determined by measuring the weight of diamond removed from the PDC cutter 100 (FIG. 3) through chipage. Alternatively, other methods known to persons having ordinary skill in the art can be used to determine the impact resistance using the VBM test.

The target cylinder 500 is able to test for both abrasive wear resistance and impact robustness of cutters 100 (FIG. 1) with a minimum consumption of time, target material, and test cutters. The target cylinder 500 can be made according to the same construction each time giving the test repeatability and continuity over the testing of numerous different cutter types. According to some exemplary embodiments, the target cylinder 500 is entirely made from hardened abrasive slurry, or soft material 560. In these exemplary embodiments, tests runs can be performed to establish abrasive wear test baselines. The formulation of the soft material 560 is maintained over time to ensure the test results are comparative over time.

Figure 6:
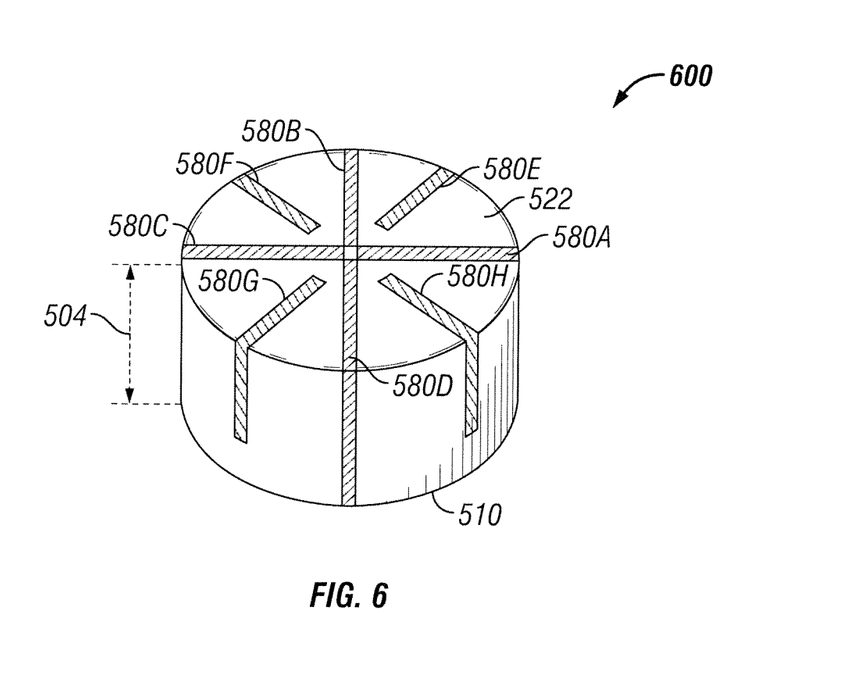
FIG. 6 shows a top perspective view of a target cylinder in accordance with an alternative exemplary embodiment of the invention.

FIG. 6 shows a top perspective view of a target cylinder 600 in accordance with an alternative exemplary embodiment of the invention. Target cylinder 600 is similar to target cylinder 500 except that additional hard material 580E, 580F, 580G, and 580H are positioned within the target cylinder 600 and extend from the exposed portion 522 to a distance that is a portion of the height 504. The exposed portion 522 is substantially planar. Hard material 580E is positioned between hard materials 580A and 580B so that it substantially bisects the angle formed between hard materials 580A and 580B. Similarly, hard material 580F is positioned between hard materials 580B and 580C so that it substantially bisects the angle formed between hard materials 580B and 580C. Similarly, hard material 580G is positioned between hard materials 580C and 580D so that it substantially bisects the angle formed between hard materials 580C and 580D. Also, hard material 580H is positioned between hard materials 580D and 580A so that it substantially bisects the angle formed between hard materials 580D and 580A. Hence, hard materials 580 are positioned in a "spoke-like" pattern. Although additional hard material 580E, 580F, 580G, and 580H extend from the exposed portion 522 to a distance that is a portion of the height 504, at least one of additional hard material 580E, 580F, 580G, and 580H can extend from the exposed portion 522 to the first end 510 without departing from the scope and spirit of the exemplary embodiment. The alternative exemplary embodiments presented with respect to target cylinder 500 also apply to target cylinder 600. For example, one or more of the hard materials 580A, 580B, 580C, 580D, 580E, 580F, 580G, and 580H can be made of different hard materials.

Figure 7:
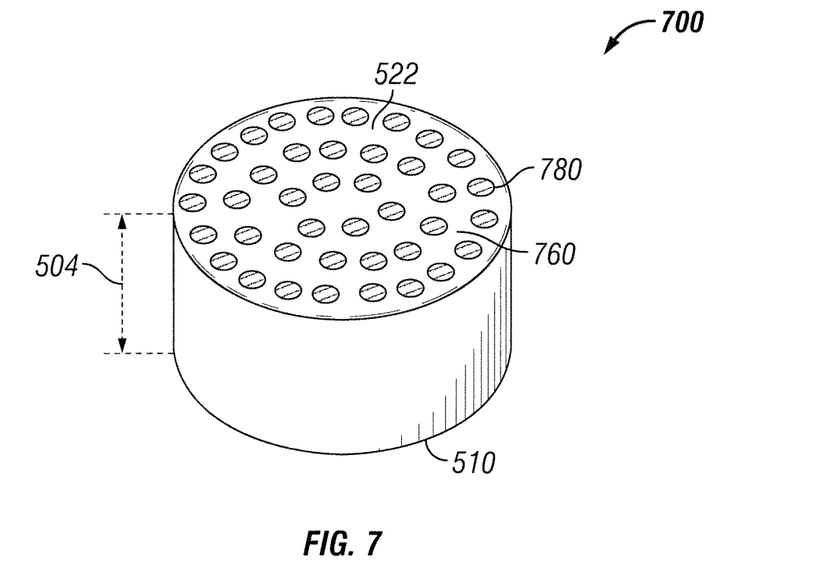
FIG. 7 shows a top perspective view of a target cylinder in accordance with a second alternative exemplary embodiment of the invention.

FIG. 7 shows a top perspective view of a target cylinder 700 in accordance with a second alternative exemplary embodiment of the invention. Target cylinder 700 is similar to target cylinder 500 (FIG. 5) except that the shape and positioning of the hard material 780 is different than the shape and positioning of the hard material 580A, 580BF, 580C, and 580D (FIG. 5). Referring to FIG. 7, the target cylinder 700 includes a soft material 760 and a hard material 780 that is positioned in a predetermined pattern along the exposed portion 522, wherein the hard material 780 is adjacent to and intervening within the soft material 760. The fabrication of the target cylinder 700 is repeatable so that an initially formed target cylinder 700 is substantially similar to a subsequently formed target cylinder 700. The predetermined pattern for the hard material 780 is repeatable so that the test results can be compared between tests conducted over time. The soft material 760 is similar to the soft material described with respect to soft material 560 (FIG. 5). Similarly, hard material 780 is similar to the hard material described with respect to hard material 580 (FIG. 5). According to FIG. 7, the hard material 780 is a cylindrical granite column that extends from the exposed portion 522 to the first end 510. In this exemplary embodiment, forty hard materials 780 are positioned within the target cylinder 700 in a predetermined pattern and are surrounded by the soft material 760. However, greater or fewer hard materials 780 can be used without departing from the scope and spirit of the exemplary embodiment. According to some alternative exemplary embodiments, the hard material 580 extends from the exposed portion 522 to a distance that is a portion of the height 504 without departing form the scope and spirit of the exemplary embodiment. In using this target cylinder 700, the PDC cutters 100 (FIG. 3) are subjected to glancing blows against the hard material 780 rather than straight on impacts that occur when using target cylinders 500 and 600 (FIGS. 5 and 6). The alternative exemplary embodiments presented with respect to target cylinder 500 (FIG. 5) also applies to target cylinder 700. For example, one or more of the hard materials 780 can be made of different hard materials.

Figure 8:
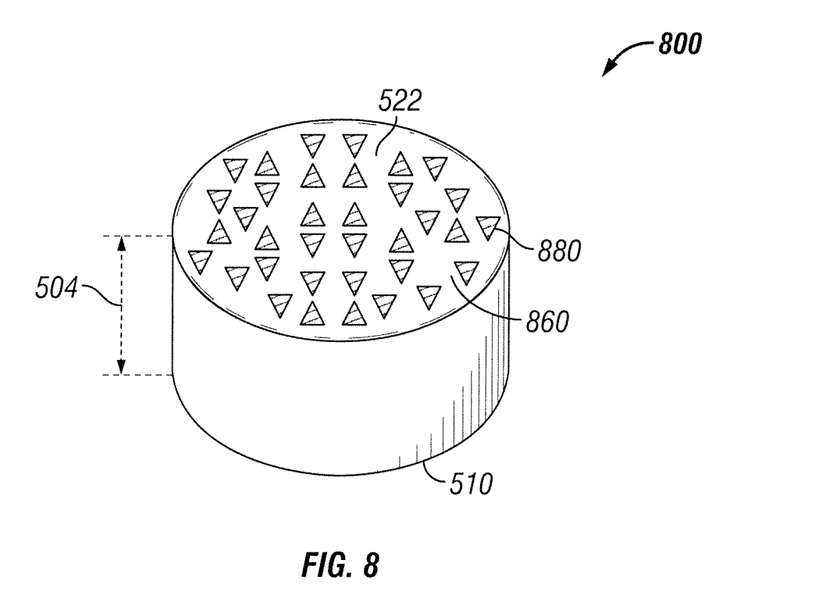
FIG. 8 shows a top perspective view of a target cylinder in accordance with a third alternative exemplary embodiment of the invention.

FIG. 8 shows a top perspective view of a target cylinder 800 in accordance with a third alternative exemplary embodiment of the invention. Target cylinder 800 is similar to target cylinder 700 (FIG. 7) except that the shape and positioning of the hard material 880 is different than the shape and positioning of the hard material 780 (FIG. 7). Referring to FIG. 8, the target cylinder 800 includes a soft material 860 and a hard material 880 that is positioned in a predetermined pattern along the exposed portion 522, wherein the hard material 880 is adjacent to and intervening within the soft material 860. The fabrication of the target cylinder 800 is repeatable so that an initially formed target cylinder 800 is substantially similar to a subsequently formed target cylinder 800. The soft material 860 is similar to the soft material described with respect to soft material 560 (FIG. 5). Similarly, hard material 880 is similar to the hard material described with respect to hard material 580 (FIG. 5). According to FIG. 8, the hard material 880 is a triangular granite column that extends from the exposed portion 522 to the first end 510. In this exemplary embodiment, thirty-three hard materials 880 are positioned within the target cylinder 800 in a predetermined pattern and are surrounded by the soft material 860. However, greater or fewer hard materials 880 can be used without departing from the scope and spirit of the exemplary embodiment. According to some alternative exemplary embodiments, the hard material 880 extends from the exposed portion 522 to a distance that is a portion of the height 504 without departing form the scope and spirit of the exemplary embodiment. The alternative exemplary embodiments presented with respect to target cylinder 500 (FIG. 5) also applies to target cylinder 800. For example, one or more of the hard materials 880 can be made of different hard materials.

Figure 9:
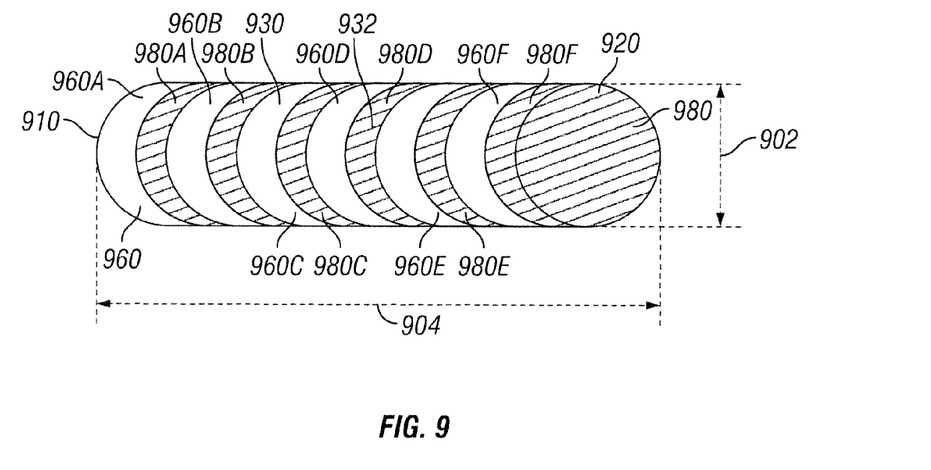
FIG. 9 shows a side perspective view of a target cylinder in accordance with a fourth alternative exemplary embodiment of the invention.

FIG. 9 shows a side perspective view of a target cylinder 900 in accordance with a fourth alternative exemplary embodiment of the invention. Referring to FIG. 9, the target cylinder 900 is a cylindrically shaped log and includes a first end 910, a second end 920, and a sidewall 930 extending from the first end 910 to the second end 920. According to this exemplary embodiment, the sidewall 930 is also referred to as an exposed portion 932 of the target cylinder 900 because the sidewall 930 is subjected to contact with the superhard component 100 (FIG. 1) when the testing is performed. The target cylinder 900 has a diameter 902 of approximately six inches and a height 904 of approximately two feet. However, in alternate exemplary embodiments, the diameter 902 can range from about four inches to about six feet without departing from the scope and spirit of the exemplary embodiment. Additionally, in alternate exemplary embodiments, the height 904 can range from about one inch to about twenty feet without departing from the scope and spirit of the exemplary embodiment.

The target cylinder 900 includes a soft material 960 and a hard material 980 that is positioned in a predetermined pattern along the exposed portion 932, where the hard material 980 is adjacent to the soft material 960. The fabrication of the target cylinder 900 is repeatable so that an initially formed target cylinder 900 is substantially similar to a subsequently formed target cylinder 900. The predetermined pattern for the hard material 980 is repeatable so that the test results can be compared between tests conducted over time. According to FIG. 9, the hard material 980 is a granite band that is about two inches wide and has a outer diameter equal to the target cylinder's 900 diameter 902. Although this exemplary embodiment uses a granite band that is two inches wide, the width of the band can vary from about one-half inch to about twelve inches in other exemplary embodiments or can also vary in width from one band to another without departing from the scope and spirit of the exemplary embodiment. Hard material 980 is similar to hard material 580 (FIG. 5), as previously described.

The soft material 960 is a cement-like band that is about two inches wide and has a outer diameter equal to the target cylinder's 900 diameter 902. Although this exemplary embodiment uses a cement-like band that is two inches wide, the width of the band can vary from about one-half inch to about twelve inches in other exemplary embodiments or can also vary in width from one band to another without departing from the scope and spirit of the exemplary embodiment. Soft material 960 is similar to soft material 560 (FIG. 5), as previously described.

According to FIG. 9, target cylinder 900 is formed using six soft materials 960A, 960B, 960C, 960D, 960E, and 960F and six hard materials 980A, 980B, 980C, 980D, 980E, and 980F. The hard materials 980A, 980B, 980C, 980D, 980E, and 980F are coupled to the soft materials 960A, 960B, 960C, 960D, 960E, and 960F in an alternating manner. In this exemplary embodiment, hard materials 980A, 980B, 980C, 980D, 980E, and 980F are fabricated from the same material. However, according to certain alternative exemplary embodiments, one or more of hard materials 980A, 980B, 980C, 980D, 980E, and 980F can be made from a different hard material. Thus, each of hard materials 980A, 980B, 980C, 980D, 980E, and 980F can be made from a different hard material or one or more of hard materials 980A, 980B, 980C, 980D, 980E, and 980F can be made from the same hard material without departing from the scope and spirit of the exemplary embodiment.

Similarly, in this exemplary embodiment, soft materials 960A, 960B, 960C, 960D, 960E, and 960F are fabricated from the same material. However, according to certain alternative exemplary embodiments, one or more of soft materials 960A, 960B, 960C, 960D, 960E, and 960F can be made from a different soft material. Thus, each of soft materials 960A, 960B, 960C, 960D, 960E, and 960F can be made from a different soft material or one or more of soft materials 960A, 960B, 960C, 960D, 960E, and 960F can be made from the same soft material without departing from the scope and spirit of the exemplary embodiment.

The surface area of the target cylinder's 900 exposed portion 932 is a combination of the soft material 960 and the hard material 980. In one exemplary embodiment, the percentage range of soft material 960 is about five percent to about ten percent, while the percentage range of hard material 980 is about ninety percent to about ninety-five percent. In another exemplary embodiment, the percentage range of soft material 960 is about ten percent to about twenty-five percent, while the percentage range of hard material 980 is about seventy-five percent to about ninety percent. In another exemplary embodiment, the percentage range of soft material 960 is about twenty percent to about thirty-five percent, while the percentage range of hard material 980 is about sixty-five percent to about eighty percent. In another exemplary embodiment, the percentage range of soft material 960 is about thirty percent to about forty-five percent, while the percentage range of hard material 980 is about fifty-five percent to about seventy percent. In another exemplary embodiment, the percentage range of soft material 960 is about forty percent to about fifty-five percent, while the percentage range of hard material 980 is about forty-five percent to about sixty percent. In another exemplary embodiment, the percentage range of soft material 960 is about fifty percent to about sixty-five percent, while the percentage range of hard material 980 is about thirty-five percent to about fifty percent. In another exemplary embodiment, the percentage range of soft material 960 is about sixty percent to about seventy-five percent, while the percentage range of hard material 980 is about twenty-five percent to about forty percent. In another exemplary embodiment, the percentage range of soft material 960 is about seventy percent to about eighty-five percent, while the percentage range of hard material 980 is about fifteen percent to about thirty percent. In another exemplary embodiment, the percentage range of soft material 960 is about eighty percent to about ninety percent, while the percentage range of hard material 980 is about ten percent to about twenty percent. In another exemplary embodiment, the percentage range of soft material 960 is about ninety percent to about ninety-five percent, while the percentage range of hard material 980 is about five percent to about ten percent.

The target cylinder 900 is formed by obtaining a casting form (not shown) and loading the casting form from bottom to top with alternating bands of soft material 960 and hard material 980. Each time the soft material 960 is loaded into the casting form, the soft material 960 is allowed to cool and harden before loading the hard material 980 above the soft material 960. According to one exemplary embodiment, the casting form is cylindrical. Once the desired number of bands are formed and the desired height of the target cylinder 900 is formed, the casting form is removed and the exposed portion 932 is smoothened.

Once target cylinder 900 is formed, the target cylinder 900 can be used in the granite log test as described above. The target cylinder's 900 first end 910 is coupled to the chuck 210 (FIG. 2) and the second end 920 is coupled to the tailstock 220 (FIG. 2), thereby positioning the exposed portion 932 adjacent the tool post 230 (FIG. 2) that has the cutter 100 (FIG. 2) mounted therein. Upon performing the granite log test using target cylinder 900, the abrasive wear resistance and/or the impact resistance for the PDC cutter 100 (FIG. 2) can be determined. During the test, the cutter 100 (FIG. 2) repeatedly makes transitions between higher compressive strength material, or hard material 980, and lower compressive strength material, or soft material 960. Each time the cutter 100 (FIG. 2) engages the end of one of the hard material 980, a front impact load is imparted to the cutting table 120 (FIG. 1) and substrate 110 (FIG. 1) as it passes across the hard material 980. When the cutter 100 (FIG. 2) exits hard material 980 and enters the soft material 960, the compressive stress on the cutting table 120 (FIG. 1) is unloaded or released, thereby creating a rebound test of the substrate 110 (FIG. 1) to the cutting table 120 (FIG. 1) at the contact face 115 (FIG. 1).

The abrasive wear resistance is determined as a wear ratio, which is defined as the volume of target cylinder 900 that is removed to the volume of the PDC cutter 100 (FIG. 2) that is removed. Alternatively, instead of measuring volume, the distance that the PDC cutter 100 (FIG. 2) travels across the target cylinder 900 can be measured and used to quantify the abrasive wear resistance for the PDC cutter 100 (FIG. 2). Alternatively, other methods known to persons having ordinary skill in the art can be used to determine the wear resistance using the granite log test. Impact resistance for the PDC cutter 100 (FIG. 2) also can be determined using the same test by measuring the volume of rock removed from the PDC cutter 100 (FIG. 2) through chipage. Alternatively, the impact resistance for the PDC cutter 100 (FIG. 2) can be determined by measuring the weight of rock removed from the PDC cutter 100 (FIG. 2) through chipage. Alternatively, other methods known to persons having ordinary skill in the art can be used to determine the impact resistance using the granite log test.

The target cylinder 900 is able to test for both abrasive wear resistance and impact robustness of cutters 100 (FIG. 1) with a minimum consumption of time, target material, and test cutters. The target cylinder 900 can be made according to the same construction each time giving the test repeatability and continuity over the testing of numerous different cutter types. According to some exemplary embodiments, the target cylinder 900 is entirely made from hardened abrasive slurry, or soft material 960. In these exemplary embodiments, tests runs can be performed to establish abrasive wear test baselines. The formulation of the soft material 560 is maintained over time to ensure the test results are comparative over time.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. An apparatus for testing wear resistance of a superhard cutter, comprising:
   a rotating table;
   a target cylinder mounted on the rotating table and comprising:
      a soft material extending from a first end of the cylinder to a second end of the cylinder; and
      a plurality of elements made from a hard material and positioned about the soft material in a pattern so that the cutter repeatedly transitions between the soft material and the hard material during testing; and
   a tool holder for receiving the cutter, for engaging the cutter with the target cylinder, and for moving the cutter relative to the target cylinder.

2. The apparatus of claim 1, wherein:
   the soft material is concrete comprising cement mixed with grains of abrasive material, and
   the hard material is rock.

3. The apparatus of claim 2, wherein the rock is granite.

4. The apparatus of claim 2, wherein the grains are quartzite.

5. The apparatus of claim 2, wherein:
   the soft material has a first unconfined compressive strength,
   the hard material has a second unconfined compressive strength, and
   a differential between the second strength and the first strength is at least 4,000 psi.

6. The apparatus of claim 1, wherein the elements are slabs.

7. The apparatus of claim 6, wherein:
   each element extends from an outer surface of the cylinder to a center thereof, and
   the pattern is an X-like pattern.

8. The apparatus of claim 6, wherein:
   each element extends from an outer surface of the cylinder toward a center thereof, and
   the pattern is a spoke-like pattern.

9. The apparatus of claim 1, wherein each element extends from the first end of the cylinder to the second end of the cylinder.

10. The apparatus of claim 1, wherein the elements are cylinders.

11. The apparatus of claim 1, wherein the elements are triangular.

12. The apparatus of claim 1, wherein:
    the first end of the cylinder is exposed to the cutter, and
    the soft material occupies more than fifty percent of a surface area of the first end.

\* \* \* \* \*